United States Patent [19]

Beck et al.

[11] 4,061,671
[45] Dec. 6, 1977

[54] ANALOGUES OF PROSTAGLANDINS

[75] Inventors: Gerhard Beck, Frankfurt am Main; Rudolf Kunstmann, Hofheim, Taunus; Milos Babej, Frankfurt am Main; Hermann Teufel, Kelkheim, Taunus, all of Germany

[73] Assignee: Hoechst Aktiengesellschaft, Frankfurt am Main, Germany

[21] Appl. No.: 563,973

[22] Filed: Apr. 1, 1975

[30] Foreign Application Priority Data

Apr. 3, 1974 Germany .............................. 2416193

[51] Int. Cl.² .......................................... C07C 177/00
[52] U.S. Cl. ........................ 260/514 D; 260/343.3 R; 260/346.22; 542/426; 424/305; 424/317; 560/121
[58] Field of Search ....................... 260/408 D, 514 D

[56] References Cited

U.S. PATENT DOCUMENTS 3,816,393  6/1974  Hayashi ................................ 260/207

FOREIGN PATENT DOCUMENTS 7,209,738  4/1976  Netherlands .......................... 260/468
1,345,934  2/1974  United Kingdom ................. 260/468

Primary Examiner—Robert Gerstl
Attorney, Agent, or Firm—Curtis, Morris & Safford

[57] ABSTRACT

The present invention relates to analogues of prostanoic acids of the formula I

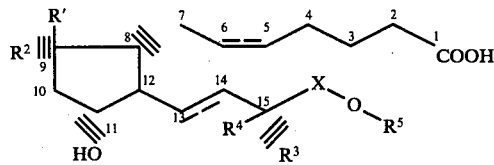

their physiologically acceptable salts with organic and inorganic bases, their esters with aliphatic, cycloaliphatic or araliphatic alcohols and to a process for the manufacture of these compounds.

The compounds according to the invention have valuable pharmacological properties and can be used as medicaments.

3 Claims, No Drawings

ANALOGUES OF PROSTAGLANDINS

Prostaglandins are a group of natural substances which have been isolated from various animal tissues. They are responsible for a large number of physiological effects in mammals. The natural prostaglandins have a carbon skeleton of generally 20 C atoms and differ chiefly in a greater or smaller number of hydroxyl groups or double bonds in the cyclopentane ring (in respect to the structure and action of prostaglandins, see inter alia M. F. Cuthbert "The Prostaglandins, Pharmacological and Therapeutic advances," William Heinemann Medical Books Ltd., London 1973).

The synthesis of analogues of prostane acids which do not occur naturally and in which the large number of pharmacological actions of the natural prostane acids are differentiated, acquires an increasing importance.

The present invention relates to new analogues which do not occur naturally, of prostanoic acids of the formula I

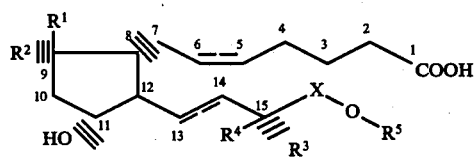

which comprises both the optically active compounds of the natural configuration and the racemic compounds and in which: $R^1$ and $R^2$ conjointly denote oxygen or each denote hydrogen or a hydroxyl group, $R^1$ and $R^2$ being different, $R^3$ and $R^4$ each denote hydrogen or a hydroxyl group, $R^3$ and $R^4$ being different, $R^5$ denotes a saturated or unsaturated, straight-chain or branched alkyl radical having 1 – 8 C atoms, a straight-chain or branched oxo-alkyl radical having 2 – 8 C atoms or the ethylene glycol acetal or ethylene thioglycol acetal thereof, a straight-chain or branched hydroxyalkyl radical having 2 – 8 C atoms, the OH group being terminal, or a straight-chain or branched carboxyalkyl radical having 2 – 8 C atoms, X denotes a linear or branched alkylene radical having 1 – 5 C atoms or an aryl, benzyl or furfuryl radical which, in turn, can be substituted by one or more alkyl groups having 1 – 3 C atoms, and wherein the C atoms 5 and 6 as well as 13 and 14 are either all bound by single bonds or all bound by double bonds, and their physiologically acceptable salts with organic and inorganic bases as well as their esters with aliphatic, cycloaliphatic or araliphatic alcohols having 1-8 C atoms. The invention further relates to a process for the manufacture of the new analogues which do not occur naturally, of prostanoic acids of the formula I, to their physiologically acceptable salts with organic and inorganic bases and to their alkyl esters having 1 – 8 carbon atoms in the ester portion as well as to pharmaceutical preparations containing these active compounds.

The process is characterised in that a. the primary bicyclic alcohol of the formula II

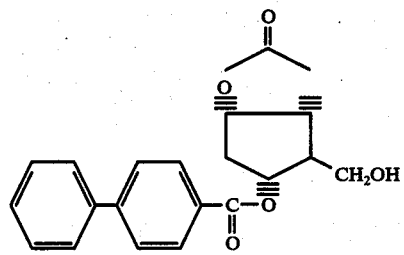

is oxidized by means of an oxidizing agent in an aprotic solvent in an inert atmosphere to give an aldehyde of the formula III

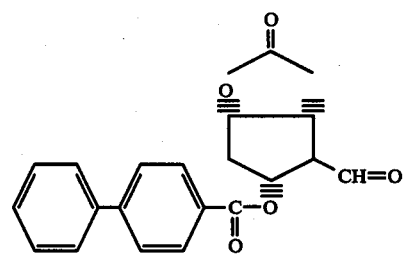

b. the resulting aldehyde of the formula III is reacted with a phosphonate of the formula IV

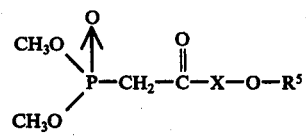

wherein X and $R^5$ have the same meaning as in the formula I, to give an unsaturated ketone of the formula V

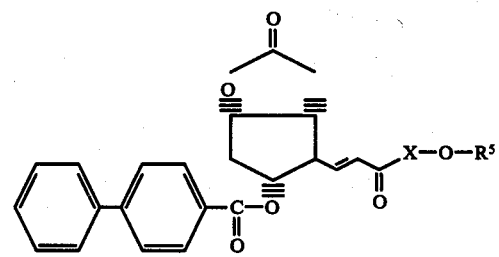

c. the resulting keton of the formula V is reduced by means of a complex metal hydride to the epimeric mixture of the alcohols of the formula VI

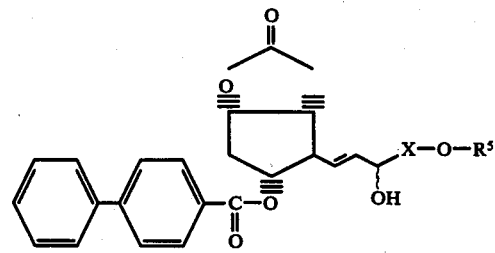

wherein X and $R^5$ have the same meaning as in formula V, d. the resulting alcohol of the formula VI, as a mixture of epimers or, after separation of the epimers, as a pure S-epimer or R-epimer, is converted by means of an anhydrous alkali metal carbonate or alkaline earth metal carbonate in an alcoholic medium at room temperature into a diol of the formula VII

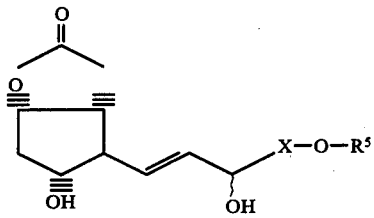

VII wherein X and R⁵ have the same meaning as in formula I, e. the resulting diol of the formula VII is converted, by the acid-catalysed addition of 2,3-dihydropyrane, into a di-tetrahydropyranyl-ether of the formula VIII

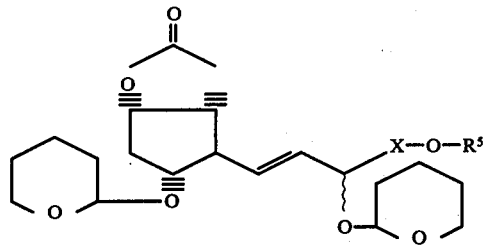

VIII wherein X and R⁵ have the same meaning as in the formula I, f. the resulting tetrahydropyranyl ether of the formula VIII is reduced by means of a complex aluminum hydride in an aprotic solvent to give a lactol of the formula IX

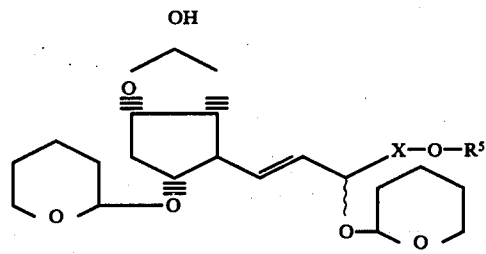

IX wherein X and R⁵ have the same meaning as in formula I, g. the resulting lactol of the formula IX is reacted with the ylide of 4-carboxy-butyltriphenylphosphonium bromide in a solution of sodium hydride in dimethylsulphoxide in an inert atmosphere to give an acid of the formula X

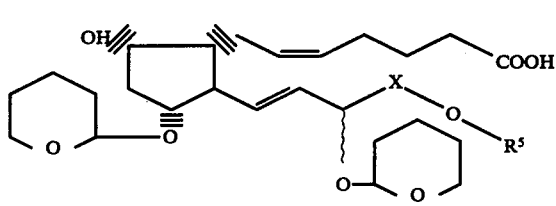

X wherein X and R⁵ have the same meaning as in the formula I, h. if appropriate, the resulting compound of the formula X is oxidized by means of an oxidizing agent to give a compound of the formula XI

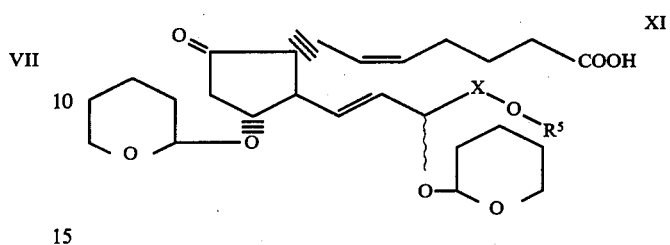

XI wherein X and R⁵ have the same meaning as in formula I, and i. the tetrahydropyranyl protective groups in a compound of the formula X or XI are split off by acid hydrolysis and the resulting compound of the formula I is optionally hydrogenated to give a compound of the formula I in which single bonds are present in he 5(6)-position and in the 13(14)-position, and, if desired, the compound of the formula I in which either single bonds in each case or double bonds in each case are present in both the 5(6)-position and in the 13(14)-position, is converted into a physiologically acceptable salt or an ester.

Of the radicals mentioned for the substituent R⁵, the methyl, ethyl, propyl and isobutyl groups are preferred, if R⁵ denotes a saturated, straight-chain or branched radical, and also the allyl radical if R⁵ denotes an unsaturated, straight-chain radical. Particularly suitable representatives of the oxo-alkyl radicals mentioned are the straight-chain or branched $C_2$ - $C_5$ oxo-alkyl radicals having terminal oxo groups, preferably the 3-oxo-propyl radical and the 2-dimethyl-3-oxo-propyl radical and oximes and oxime-ethers thereof. Particularly suitable representatives of the hydroxyalkyl radicals are the straight-chain or branched $C_2$ - $C_5$ hydroxyalkyl radicals, preferably the 3-hydroxypropyl radical and the 2-dimethyl-3-hydroxypropyl radical, and particularly suitable representatives of the carboxyalkyl radicals are the straight-chain or branched $C_2$ - $C_5$ carboxyalkyl radicals, preferably the 2-carboxyethyl radical and the 2-dimethyl-2-carboxyethyl radical. Of the radicals mentioned for X, preferably the methylene group or a branched alkyl radical of 2 - 5 carbon atoms is used, especially the ethylidene group as well as the isomeric isopropylene and isobutylene groups possible with regard to the bonds. Especially preferred are the compounds of the formula I, in which $R_1$ and $R_2$ together stand for oxygen and which contain double bonds in 5(6)-position and in 13(14)-position.

The process according to the invention starts from a primary bicyclic alcohol of the formula II which is already known and which can be prepared by the method of E. J. Corey et al. (J. Am. Chem. Soc. 93, 1491 - 1493 (1971)).

In the first stage of the process according to the invention, such an alcohol is oxidized to the aldehyde of the formula III by means of an oxidizing agent, preferably by means of a complex composed of thioanisole and chlorine or the complex compound composed of $CrO_3$ and pyridine in an aprotic solvent at temperatures between $-50°$ C and room temperature, preferably between $-30°$ and $-5°$ C, in an inert atmosphere. Examples of solvents which can be used for this purpose are aromatic hydrocarbons, such as benzene or toluene, or chlorinated aliphatic hydrocarbons, such as carbon tetrachloride.

In the next stage, the resulting aldehyde of the formula III is reacted by the method of Horner, Wittig and Emmons with a phosphonic acid ester of the formula IV to give an unsaturated ketone of the formula V, a preferred embodiment of the reaction consists in preparing the sodium salt of the phosphonic acid ester by means of sodium hydride in glycol dimethyl ether, then adding an aldehyde of the formula III and allowing reaction to take place at room temperature for 2 to 6 hours.

The phosphonic acid esters of the formula IV can be prepared by reacting an ester of the formula $R^5$—OX—$CO_2$—alkyl in the presence of excess butyl-lithium and methylphosphonic acid dimethyl ester (for example by the method of Corey, J. Am. Chem. Soc. 88, 5654 (1966)).

The epimeric mixture of the alcohols of the formula VI is obtained from the ketone of the formula V by reduction with a complex metal hydride, preferably with an alkali metal boranate or zinc boranate in ethereal solution, preferably at temperatures between 0° C and room temperature. The zinc boranate is preferably prepared in situ from zinc chloride and sodium borohydride in absolute ethereal solution.

If X denotes the furfuryl radical, the ketone of the formula V, in which a Δ13(14) double bond is present, is converted, by using an excess of alkali metal boranate at temperatures between —10° and —5° C, into an alcohol of the formula VIa

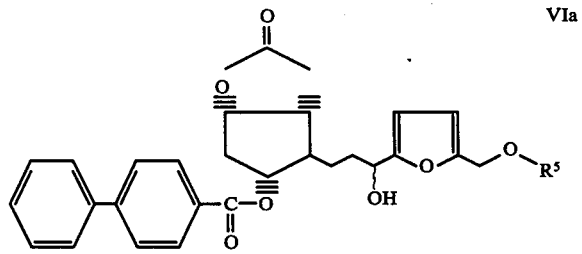

VIa wherein $R^5$ has the same meaning as in formula I.

The alcohols of the formula VI are particularly suitable for separation into the S-epimers and R-epimers, preferably by means of column chromatography on silica gel, but the further action can also be carried out with the mixture of epimers and the separation of the epimers can be carried out at the stage of the end product.

The subsequent hydrolytic splitting off of the p-phenylbenzoyl group of the alcohol of the formula VI is carried out in an alcoholic medium with the aid of alkali metal carbonates or alkaline earth metal carbonates. An advantageous embodiment consists of treating the alcohol or the corresponding mixture of epimers in absolute methanol at room temperature with anhydrous potassium carbonate, a diol of the formula VII being formed.

The di-tetrahydropyranyl ether of the formula VIII is prepared in an ethereal or benzene solution of the alcohols of the formula VII in the presence of customary acid catalysts, such as, for example, toluenesulphonic acid.

The compound of the formula VIII is reduced to a lactol of the formula IX by means of a complex aluminum hydride in an aprotic solvent. It is preferable to use diisobutyl-aluminum hydride in toluene at —60° to —70° C.

The resulting lactone of the formula IX can be reacted by the method of Wittig, without further purification, to give a carboxylic acid of the formula X. The preferred embodiment of this process follows the instructions given in J. Org. Chem. 28, 1128 (1963).

In order to prepare a prostaglandin of the E-series, a compound of the formula X is oxidized at temperatures of —40° to 0° C, preferably with Jones's reagent (a solution of chromium-(VI) oxide in sulphuric acid) in acetone or with a complex compound of chromium-(VI) oxide with pyridine in methylene chloride as the solvent, at —20° C. The resulting compound of the formula XI is separated off by extraction and, if necessary, is purified by column chromatography.

The protective ether groups in a compound of the formula X or XI are split off by mild acid hydrolysis of the tetrahydropyranyl ether groups by means of aqueous organic acids, preferably in 2% strength aqueous-alcoholic oxalic acid solution at 20° to 50° C, or by heating for 1 to 2 hours in 60 to 70% strength acetic acid at 40° C, a carboxylic acid of the formula I being formed in which a double bond is present in each of the 5(6)- and 13(14)-positions.

In order to prepare a prostaglandin of the tetrahydro-E or of the tetrahydro-F series, a compound of the formula I having Δ5(6) and Δ13(14) double bonds is hydrogenated in the presence of a noble metal catalyst, a compound of the formula I having a single bond both in the 5(6)- and in the 13(14)- position being formed. In a preferred embodiment, hydrogenation is carried out at room temperature in an alcoholic solution in the presence of a catalyst consisting of 5% of palladium on carbon.

If a separation of epimers has not been carried out at the stage of the alcohols of the formula VI, a separation of the 15-S-epimer from the 15-R-epimer can preferably be carried out at the stage of a compound of the formula I, wherein $R_1$ and $R_2$ conjointly denote oxygen, or of a compound of the formula I, wherein $R_1$ and $R_2$ are different and each denote hydrogen or the hydroxyl group. In this process, the separation is preferably carried out on silica gel (Merck ®, 70 - 230 mesh), the 15-S-epimer usually being eluted after the 15-R-epimer.

Suitable eluting agents for the separation, by column chromatography, of the compounds of the formula I wherein $R_1$ and $R_2$ conjointly denote oxygen, are mixtures of chloroform and methanol in the ratio of 15:1 to 3:2, while the separation of compounds of the formula I wherein $R_1$ and $R_2$ are different and each denote H or OH, is preferably carried out by means of a mixture of acetic acid ethyl ester and acetic acid in the ratio of 97.5:2.5.

The compounds according to the invention, of the general formula I, are analogues of prostane acids which do not occur naturally and which can be used as medicaments by virtue of their pharmacological effects.

The natural prostaglandins $PGE_{1\alpha}$, $PGE_{2\alpha}$, $PGF_{2\alpha}$ or $PGA_2$ have the disadvantage that they are so quickly deactivated in a living body that their pharmacological action cannot be maintained for the time required for the therapy.

In contrast to this, the compounds according to the invention are distinguished by a longer duration of action and a stronger effect.

The compounds according to the invention csn be used as medicaments having a hypotensive and diuretic action and a prophylactic and therapeutic action in thromboses, and a labor-inducing action, as abortifacients and contraceptives, as agents for inhibiting secretion of the gastric juices, and as agents against gastric ulcers and asthma.

They can be used as free acids, in the form of their physiologically acceptable inorganic or organic salts, or as esters of aliphatic, cycloaliphatic or araliphatic alcohols. Examples of suitable salts are benzylammonium, triethanolammonium or morpholine salts and alkali metal salts, and examples of suitable esters are preferably the esters of lower aliphatic alcohols, such as methyl, ethyl, propyl, butyl or pentyl esters or benzyl esters.

Acids, like salts or esters, can be used in the form of their aqueous solutions or suspensions or as solutions in pharmacologically acceptable organic solvents, such as, for example, monohydric or polyhydric alcohols, dimethylsulphoxide or dimethylformamide, and can also be used in the presence of pharmacologically acceptable polymeric excipients, such as, for example, polyvinylpyrrolidone.

The active substances of the invention can be administered via the oral or the parenteral (intravenous) route, by embrocation or inhalation.

Preparations which can be used are the customary galenical infusion solutions or injection solutions and tablets, as well as preparations which can be applied locally, such as creams, emulsions, suppositories or aerosols.

The daily dosage is allowed to be 1 mcg to 1 mg per kg of body weight, the dosage unit to be 0.05 mg to 200 mg of the active substances of the invention.

The compounds can be used on their own or conjointly with other pharmacological active substances, such as, for example, diuretics or antidiabetics.

The compounds of the formulae III, V, VI, VII, VIII, IX, X and XI are valuable intermediate products for the synthesis of the compounds according to the invention, of the formula I.

In a manner analogous to the manufacturing Examples, the following compounds are preferably prepared:

9-Oxo-11α, 15-dihydroxy-16, 16-dimethyl-18-oxa-5-cis, 13-trans, 20, -20-homo-prostatrienoic acid 9-Oxo-11α, 15-dihydroxy-16,19,19-trimethyl-17-oxo-5-cis, 13-trans-prostadienoic acid 9α, 11α, 15-Trihydroxy-16,19,19-trimethyl-17-oxa-5-cis, 13-trans-prostadienoic acid 9-Oxo-11α, 15-dihydroxy-16,19,19-trimethyl-17-oxa-prostanoic acid 9α,11α, 15-Trihydroxy-16,19,19-trimethyl-17-oxa-prostanoic acid 9-Oxo-11α, 15-dihydroxy-16, 16-dimethyl-18-oxa-20-homo-prostanoic acid 9α, 11α, 15-Trihydroxy-16, 16-dimethyl-18-oxa-20-homo-prostanoic acid 9-Oxo-11α, 15-dihydroxy-16, 16-dimethyl-18-oxa-20-nor-prostanoic acid 9α, 11α, 15-Trihydroxy-16, 16-dimethyl-19-oxa-20-nor-prostanoic acid 9-Oxo-11α, 15-dihydroxy-16, 16, 20, 20-tetramethyl-18-oxa-prostanoic acid 9α, 11α, 15-Trihydroxy-16, 16, 20, 20-tetramethyl-18-oxa-prostanoic acid

EXAMPLES

EXAMPLE 1

Synthesis of 2-oxa-3-oxo-6-syn-formyl-7-anti-p-biphenyl-carboxy-cis-bicyclo[3,3,0]octane (III)

1.34 l of a solution of 21.3g of $Cl_2$ in 1.5 l of absolute $CCl_4$ are introduced, under argon, into a 2 l four-necked flask and are cooled to $-10°$ C, and 33.3 g of thioanisole are added dropwise, a white precipitate being thrown down.

After the addition is complete, the mixture is cooled to $-20°$ C and stirred for 30 minutes. Meanwhile, a solution of 30 g of lactone-alcohol (II) in at most 300 ml of absolute $CH_2Cl_2$ is prepared. This solution is added dropwise rapidly at $-20°$ C and the mixture is subsequently stirred for 2 - 3 hours at $-20°$ C. 54.3 g of triethylamine dissolved in 50 ml of absolute $CH_2Cl_2$ are then added dropwise slowly over the course of 1 hour, it being permissible for the temperature to rise to $-5°$ C towards the end of the dropwise addition.

The reaction mixture is then poured into an ice cooled solution of 600 ml of 1% strength HCL and 1.5 l of diisopropyl ether. The white precipitate of 24 g which is thrown down is filtered off on as large a filter as possible and is washed with ether. The filtrate is poured into a separating funnel and the organic phase is separated off, dried and concentrated, at not more than $+15°$ C, to a volume of approx. 750 ml. After cooling well, the crystals which have precipitated are filtered off (5 g) and are combined with the filter residue.

Yield: 29 g of white crystals (98%).

Thin layer chromatogram (solvent chloroform-methanol 15:1), $R_f = 0.63$.

Nuclear resonance spectrum (in $CDCl_3$), $\delta$ - values: 1.9 - 4.0 multiplet 6 H (—$CH_2$—, >CH—), 5.0 - 5.34 triplet 1 H (—CH—OCO), 5.65 - 5.9 multiplet 3 H (—CH—OCO), 7.3 - 8.2 multiplet 9 H (aromatic protons) and 9.8 singlet 1H (CH = O).

EXAMPLE 2 a. Synthesis of dimethyl 2-oxo-3,3-dimethyl-4-ethoxy-butyl-phosphonate (IVa)

18 g of dimethyl methylphosphonate in 100 ml of tetrahydrofurane were cooled under argon to $-70°$ C. 100 ml of a 2-molar n-butyl-lithium solution in hexane are added dropwise with stirring. After 15 minutes, 20 g of 1,1-dimethyl-2-ethoxy-propionic acid methyl ester in 75 ml of tetrahydrofurane were added dropwise at $-70°$ C. The mixture was then stirred for 2 hours. It was neutralised with 12 ml of glacial acetic acid. The solvent was concentrated (sic) in vacuo, the residue was taken up in chloroform and washed with water and the chloroform phase was dried with $MgSO_4$ and concentrated and the residue was distilled in vacuo.

Yield: 10.5 g of a colourless oil IV a (37%), boiling point 108°/0.05 mm Hg.

| Elementary Analysis: | C | H | P |
|---|---|---|---|
| Calculated $C_{10}H_{21}O_5P$ | 47.6 | 8.0 | 11.6 |
| Found | 47.1 | 8.6 | 11.1 |

Nuclear magnetic resonance (in $CDCl_3$), $\delta$ - values: 1.1 triplet 3 H (—$CH_2CH_3$) J = 7 Hz, 1.12 singlet 6 H ($CH_3$), 3.25 doublet 2H (CO—$CH_2$—P(o)<) J = 20 Hz, 3.5 quartet 2 H (—CH$_2$CH$_3$) J = 7 Hz, 3.8 doublet 6 H (OCH$_3$).

The compounds IV b to IV d were also prepared in the same way.

b. Dimethyl 2-oxo-2-(5'-methoxymethylfuryl)-ethylphosphonate (IV b)

On treatment with 100 ml of 2-molar butyl-lithium solution in hexane and with 25.2 g of 2-methoxymethyl-furane-5-carboxylic acid methyl ester, 21.3 g of dimethyl methylphosphonate gave: 24 g of a pale yellow oil (61.5% yield), boiling point 167° C/0.1 mm Hg.

| Elementary Analysis: | C | H | P |
|---|---|---|---|
| Calculated C$_{10}$H$_{15}$O$_6$P | 45.8 | 5.7 | 11.8 |
| Found | 45.9 | 5.8 | 11.4 |

Nuclear magnetic resonance (in CDCl$_3$), δ - values: 3.2 singlet 3 H (CH$_2$OCH$_3$), 3.55 doublet 2 H (—COCH$_2$P(o)<) J = 22 Hz, 3.8 doublet 6 H (OCH$_3$), 4.5 singlet 2 H (—CH$_2$OCH$_3$), 6.55 doublet 1 H (furane), 7.35 doublet 1 H (furane).

c. Dimethyl 2-oxo-3,3-dimethyl-4-allyloxy-butylphosphonate (IV c)

On treatment with 135 ml of 2-molar butyl-lithium solution in hexane and with 13 g of 1,1-dimethyl-2-allyloxypropionic acid methyl ester, 50.0 g of dimethyl phosphonate gave: 9.8 g of a pale yellow oil (49.5% yield), boiling point 136° C/0.2 mm Hg.

| Elementary Analysis: | C | H | P |
|---|---|---|---|
| Calculated C$_{11}$H$_{21}$O$_5$P | 50.0 | 7.9 | 11.8 |
| Found | 50.1 | 7.8 | 11.3 |

Nuclear magnetic resonance (in CDCl$_3$), δ - values: 1.2 singlet 6 H (CH$_3$), 3.25 doublet 2 H (CO—CH$_2$—P-(O)<) J = 21 Hz, 3.45 singlet 2 H (—CH$_2$—O—CH$_2$—C(CH$_3$)$_2$—), 3.8 doublet 6 H (OCH$_3$), 4.0 doublet 2 H (CH$_2$=CH-CH$_2$-O-), 5.0 - 6.3 multiplet 3 H (olefinic protons).

d. Dimethyl 2-oxo-3,3-dimethyl-4-isobutoxy-butylphosphonate (IV d)

On treatment with 100 ml of 2-molar butyl-lithium solution in hexane and with 28.5 g of 1,1-dimethyl-2-isobutoxy-propionic acid methyl ester, 40 g of dimethyl phosphonate gave: 20 g of a pale yellow oil (47.5% yield), melting point 123°-126° C/0.8 mm

| Elementary Analysis: | C | H | P |
|---|---|---|---|
| Calculated C$_{12}$H$_{25}$PO$_5$ | 51.4 | 8.9 | 11.1 |
| Found | 50.9 | 9.1 | 10.8 | e. Dimethyl-2-oxo-3,3-dimethyl-4-methoxy-butylphosphonate (IVe)

On treatment with 180 ml of 2-molar butyl-lithium solution in hexane and 29.2 g of 1,1-dimethyl-2-methoxy-propionic acid methyl ester, 72 g of dimethyl phosphonate gave: 29.4 g of a pale oil (68% yield), melting point 122° - 128° C/0.5 mm, n$_D^{20}$ = 1.4458

| Elementary Analysis: | C | H | P |
|---|---|---|---|
| Calculated C$_9$H$_{19}$PO$_5$ | 45.5 | 8.0 | 12.98 |
| Found: | 45.2 | 8.1 | 12.7 |

EXAMPLE 3 a. Synthesis of 2-oxa-3-oxy-6(3'-oxo-4',4'-dimethyl-6'-oxa-1'-octenyl)-7-(4"-biphenylcarbonyloxy)-bicyclo[3,3,0]octane (Va)

5 g of the phosphonate IVa are added dropwise, under argon, over the course of 15 minutes to a suspension of 0.67 g of sodium hydride (80% strength suspension oil) in 50 ml of absolute 1,2-dimethoxyethane. A solution is formed, with evolution of hydrogen. The mixture is stirred for a further 40 minutes and 7.1 g of lactone-aldehyde (III) are then added dropwise over the course of 10 minutes. The mixture is stirred for a further hour, neutralised with glacial acetic acid, clarified with a little animal charcoal, filtered and concentrated in vacuo. The residue is recrystallised from 80 ml of isopropanol. 5.1 g of the desired product were obtained in this way.

| Yield: 54%, melting point 118° C. Elementary Analysis: | C | H |
|---|---|---|
| Calculated C$_{29}$H$_{30}$O$_5$ | 75.5 | 6.8 |
| Found | 74.8 | 6.7 |

Nuclear magnetic resonance (in CDCl$_3$), δ - values: 1.1 triplet 3 H (—CH$_2$CH$_3$), 1.12 singlet 6 H (CH$_3$), 2.1 - 3.2 multiplet 6 H (—CH$_2$—, —CH—), 3.4 singlet 2 H (—(CH$_3$)$_2$C-CH$_2$O), 3.4 quartet 2 H (—OCH$_2$—CH$_3$), 4.95 - 5.55 multiplet 2 H (—HC—O—CO—), 6.65 - 6.85 multiplet 2 H (olefinic protons), 7.3 - 8.2 multiplet 9 H (aromatic protons).

Absorption in the infrared spectrum (ground with KBr): 2,920, 1,760 (lactone-carbonyl), 1,713 (ester-carbonyl), 1,658 (vinyl ketone-carbonyl), 1,625 (aromatic), 1,500, 1,270, 1,170, 970 and 740 cm$^{-1}$.

b. Synthesis of 2-oxa-3-oxy-6(3'-oxo-3'-(5"-methoxymethylfuryl)-1'-propenyl)-7-(4"-biphenylcarbonyloxy)-bicyclo[3,3,0]-octane (Vb)

5.2 g of the compound IVb were reacted with 6.55 g of lactone-aldehyde III, analogously to Va. After working up, we obtained, as the compound Vb, 4.8 g of white crystals of melting point 141° C (52%).

| Elementary Analysis: | C | H |
|---|---|---|
| Calculated C$_{29}$H$_{25}$O$_7$ | 71.7 | 5.2 |
| Found | 71.6 | 5.3 |

Nuclear magnetic resonance (in CDCl$_3$), δ - values: 2.3 - 3.2 multiplet 6 H (—CH$_2$—,>CH—), 3.42 singlet 3 H (OCH$_3$), 4.5 singlet 2 H (CH$_2$O), 5.0 - 5.7 multiplet 2 H (HC—O—CO), 6.45 - 6.65 doublet 1 H (furane), 6.95 - 7.1 doublet 2 H (olefinic protons), 7.2 - 8.2 multiplet 10 H (aromatic protons + furane).

Thin layer chromatogram (developer solution methylene chloride - methanol 4:1): R$_f$ = 0.71

Thin layer chromatography: (developing solvent methylene chloride - ethyl acetate 10:1): R$_f$: 0.50.

Absorptions in the infrared spectrum (ground with KBr): 2.940, 1,755 (lactone-carbonyl band), 1,710 (ester-carbonyl band), 1,680 (vinyl ketone-carbonyl band), 1,620 (aromatic), 1,270, 1,165, 1,105 and 740.

c. 2-Oxa-3-oxy-6(3'-oxo-4',4'-dimethyl-6'-oxa-1',8'-nonadienyl)-7-(4''-biphenylcarbonyloxy)-bicyclo[3,3,0]octane (Vc) was prepared in an analogous manner by reaction with dimethyl 2-oxo-3,3-dimethyl-4-allyloxy-butylphosphonate (IVc). White crystals of melting point 108° C (55%).

| Elementary Analysis: | C | H |
|---|---|---|
| Calculated $C_{30}H_{32}O_6$ | 73.8 | 6.5 |
| Found | 73.7 | 6.7 |

Nuclear magnetic resonance (in $CDCl_3$), δ -values: 1.10 singlet 6 H ($CH_3$), 2.0 - 3.1 multiplet 6 H (—$CH_2$—>CH—), 3.4 singlet 2 H (—$(CH_3)_2C$—$CH_2$—O—), 3.9 doublet 2 H ($CH_2$=CH—$CH_2O$—), 4.9 - 6.4 multiplet 5 H ($CH_2$=CH—, and HC—O—CO—), 6.6 - 6.9 multiplet 2 H (olefinic protons), 7.3 - 8.2 multiplet 9 H (aromatic protons).

Thin layer chromatography: (developer solution methylene chloride - ethyl acetate 10:1): $R_f$ = 0.4 d. 2-Oxa-3-oxy-6(3'-oxo-4',4'-dimethyl-6'-oxa-8'-methyl-1'-noneyl)-7-(4''-biphenylcarbonyloxy)-bicyclo[3,3,0]octane (Vd) was prepared in an analogous manner by reaction with dimethyl 2-oxo-3,3-dimethyl-4-isobutoxy-butylphosphonate (Vd). White crystals of melting point 110° C (53% yield)

| Elementary Analysis: | C | H |
|---|---|---|
| Calculated $C_{30}H_{32}O_6$ | 73.8 | 7.2 |
| Found | 73.7 | 6.9 | e. 2-Oxa-3-oxy-6(3'-oxo-4',4'-dimethyl-6'-oxa-1'-heptenyl)-7-(4''-biphenylcarbonyloxy)-bicyclo[3.3.0]octane (Ve) was prepared in an analogous manner by reaction with dimethyl-2-oxo-3,3-dimethyl-4-methoxy-butylphosphonate (IVe).

White crystals from isopropanol: (47%)

Nuclear magnetic resonance (in $CDCl_3$) δ-values: 1.1 singlet 6 H ($CH_3$), 2.0 - 3.2 multiplet 6 H (—$CH_2$—,>λCH—) 3.25 singlet 3 H ($OCH_3$), 3.4 singlet 2 H (—$OCH_2$—), 4.9 - 5.7 multiplet 2 H (>CH—OCO—), 6.6–6.8 multiplet 2H (olefinic protons), 7.3 - 8.2 multiplet 9 H (aromatic protons).

The further reactions were carried out in an analogous manner, in each case starting from the compounds Va to Ve. However, the following examples 4 to 13 only describe in a detailed form those reactions which start from compound Va.

EXAMPLE 4

Synthesis of 2-oxa-3-oxy-6-(3'-hydroxy-4',4'-dimethyl-6'-oxa-1'-octenyl)-7-(4''-biphenylcarbonyl)-bicyclo[3,3,0]octane (VI)

3.8 g of the compound Va were dissolved in 45 ml of 1,2-dimethoxyethane. 30 ml of a 0.5-molar solution of zinc borohydride (prepared as follows: 2.8 g of zinc chloride were suspended in 45 ml of 1,2-dimethoxy 1,2-dimethoxy-ethane and 1.52 g of sodium borohydride were added with cooling and stirring and the mixture was stirred for ½ hour and quickly filtered from undissolved matter under argon) were added at 0° C. The mixture was stirred for 2½ hours at room temperature. Excess of the reagent was then decomposed by means of glacial acetic acid at 0° C. The desired product was extracted with ethyl acetate- water. The organic phase was dried with $MgSO_4$, filtered and concentrated in vacuo. The yield of the compound VI was 3.65 g of a colourless oil (98%).

The 15-S and 15-R epimers can be separated easily by column chromatography with pure diethyl ether.

$R_f$-value for the 15-S-epimer in the thin layer = chromatogram (development distance of the solvent front 30 cm) (ether) = 0.28, $R_f$-value for the 15-R epimer = 0.21.

Absorptions in the infrared spectrum (without solvent): 3,450 (OH band), 2,920, 1,775 (lactone-carbonyl), 1,720 (ester-carbonyl), 1,620 (aromatic), 1,280, 1,190, 975 and 865 cm$^{-1}$.

Nuclear magnetic resonace (in $CDCl_3$), δ - values: 0.85 doublet 6 H ($CH_3$), 1.15 triplet 3 H ($CH_3CH_2$—), 2.2 - 3.0 multiplet 7 H (—$CH_2$—,—CH— and OH), 3.25 singlet 2 H (—$(CH_3)_2C$—$CH_2$—O—), 3.4 quartet 2 H (—$OCH_2CH_3$), 3.8 - 4.1 multiplet 1 H (HC—OH), 4.9 - 5.5 multiplet 2 H (—HC—O—CO—), 5.6 - 5.8 multiplet 2 H (olefinic protons), 7.3 - 8.3 multiplet 9 H (aromatic protons).

EXAMPLE 5

Synthesis of 2-oxa-3-oxy-6(3'-hydroxy-4',4'-dimethyl-6'-oxa-1'-octenyl)-7-hydroxy-bicyclo[3,3,0]octane (VII)

3.6 g of the compound VI were dissolved in 60 ml of absolute methanol. 1.2 g of very finely powdered potassium carbonate were then added at room temperature and the mixture was stirred under argon for 2½ hours. In the course thereof a crystalline precipitate of p-diphenylcarboxylic acid methyl ester was thrown down. The mixture was acidified with 1 N hydrochloric acid to pH 2 while cooling with ice, the p-diphenylcarboxylic acid methyl ester was filtered off and the filtrate was treated with ethyl acetate - water. After the extraction, the organic phase was separated off and dried with $MgSO_4$ and the solvent was removed in vacuo. The yield of the compound VII was 1.86 g of a colourless oil (83%).

Thin layer chromatogram (developer solution: methanolchloroform = 2:8): phosphomolybdic acid used as spray reagent: $R_f$ = 0.72.

Nuclear magnetic resonance (in $CDCl_3$), δ - values: 0.9 singlet 6 H ($CH_3$), 1.18 triplet 3 H ($CH_3CH_2$), 1.6 - 2.8 multiplet 6 H (—$CH_2$—, —CH—), 3.15 singlet 2 H (OH), 3.3 singlet 2 H (—$(CH_3)_2C$—$CH_2$—O—), 3.45 quartet 2 H (—O—$CH_2$—$CH_3$), 3.8 – 4.2 multiplet 2 H (—HC—OH), 4.8 - 5.1 multiplet 1 H (HC—O—CO—), 5.4 - 5.7 multiplet 2 H (olefinic H).

EXAMPLE 6

Synthesis of 2-oxa-3-oxy-6(3'-tetrahydropyranyloxy-4',4'-dimethyl-6'-oxa-1'-octenyl)-7-tetrahydropyranyloxy-bicyclo[3,3,0]octane (VIII)

1.8 g of the compound VII were dissolved in 45 ml of absolute methylene chloride and 6.3 g of 2,3-dihydropyrane and 1 ml of a 0.5% strength solution of p-toluenesulphonic acid in methylene chloride were then added. The mixture was stirred for 3 hours at room temperature and ethyl acetate was then added, followed by saturated sodium bicarbonate solution. The organic phase was separated off and dried with magnesium sulphate, and the solvent was removed in vacuo. The residue (2.9 g of a colorless oil) was submitted to column chromatography on (Merck) silica gel. Fractions 155 – 305 contained 1.81 g of a compound VIII as a colorless oil (65%).

Thin layer chromatogram (developer solution: benzene - ethyl acetate 4:1): $R_f = 0.18$.

Nuclear magnetic resonance (in CDCl$_3$), $\delta$ - values: 0.85 singlet 6 H (CH$_3$), 1.12 triplet 3 H (C$\underline{H_3}$—CH$_2$—), 1.4 – 1.7 multiplet 12 H (THP—C$\underline{H_2}$—), 1.7 – 2.8 multiplet 6 H (—C$\underline{H_2}$—, —C$\underline{H}$—), 3.2 singlet 2 H (—(CH$_3$)$_2$-C—C$\underline{H_2}$—O), 3.42 quartet 2 H (—O—C$\underline{H_2}$—CH$_3$), 3.55 – 4.2 multiplet 2 H (>C$\underline{H}$—OTHP), 4.5 – 4.8 multiplet 2 H

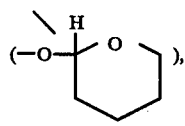

4.8 – 5.2 multiplet 1 H (—C$\underline{H}$—O—CO—), 5.4 – 5.7 multiplet 2 H (olefinic H).

EXAMPLE 7

Synthesis of 2-oxa-3-hydroxy-6(3'-tetrahydropyranyloxy-4',4'-dimethyl-6'-oxa-1'-octenyl)-7-tetrahydropyranyloxy-bicyclo[3,3,0]octane (IX)

1.72 g of the compounds VIII were dissolved in 25 ml of toluene and were then cooled to −70° C. 10 ml of a 1 M solution of diisobutyl-aluminum hydride in toluene was added dropwise over the course of 3 minutes under an atmosphere of argon. The mixture was stirred for a further 2 hours at −70° C and excess hydrogenation reagent was then decomposed with 10 ml of methanol. The reaction product was extracted with ethyl acetate and semi-saturated sodium chloride solution. The organic phase was separated off and dried with magnesium sulphate and the solvent was removed in vacuo. The yield of the compound VIII was 1.66 g of a colorless oil (95%).

Thin layer chromatogram (developer solution: benzene - ethyl acetate 4:1): $R_f = 0.06$.

Absorptions in the infrared spectrum (without solvent): 3,400 (OH band), 2,930, no carbonyl band, 1,450, 1,200 1,120, 1,030 and 980 cm$^{-1}$.

EXAMPLE 8

Synthesis of 9α-hydroxy-11α,15α-ditetrahydropyranyloxy-16,16-dimethyl-18-oxa-5-cis-13-trans-prostadienoic acid (X)

5 ml of absolute dimethylsulphoxide were added to 0.39 g of sodium hydride (80% strength suspension in oil) under argon and the mixture was stirred for 1 hour at 60° C until the evolution of hydrogen ceases. After cooling to room temperature, this solution was treated dropwise with 2.85 g of 4-carboxybutyltriphenyl-phosphonium bromide (dried at 120° C in a high vacuum) dissolved in 5 ml of absolute dimethylsulphoxide. Hereupon, the phosphorylide required for the Wittig reaction formed, and the mixture assumed an intense red coloration. The mixture was stirred additionally for 30 minutes at 30° C. 1.66g of the compound IX in 5 ml of dimethylsulphoxide were than added dropwise. The mixture was stirred for 2½ hours at room temperature and then added to ice water which was covered with diethyl ether. The neutral substances are extracted and the aqueous solution is acidified with 5% strength sodium bisulphate solution to pH 2, whilst cooling with ice, and is immediately extracted with ether. The ether solution is then extracted with 0.5 N sodium hydroxide solution and the aqeous alkaline phase is separated off and again acidified, whilst cooling with ice, and extracted with ether; the ether solution was dried with magnesium sulphate, filtered and concentrated in vacuo. The yield of the compound IX, after column chromatography on 250 g of silica gel (solvent system: ethyl acetate - acetic acid, 97.5:2.5), was 1.76 g of a slightly yellow oil (90%).

Thin layer chromatogram (developer solution: ethyl acetate - acetic acid, 97.5:2.5), $R_f = 0.56$.

Adsorptions in the infrared spectrum (without solvent): 3,400 (OH band), 2,950, 1,715 (carbonyl band), 1,440, 1,240, 1,120, 1,025 and 970 cm$^{-1}$.

EXAMPLE 9 a. Synthesis of 9α,11α,15-trihydroxy-16,16-dimethyl-18-oxa-5-cis-13-trans-prostadienoic acid (16,16-dimethyl-18-oxa-PGF$_{2\alpha}$) (IA) 15-S- and 15-R-epimer 0.88 g of the compound X is dissolved in 1 ml of tetrahydrofurane, 9 ml of a mixture of acetic acid and water in the ratio of 2:1 were then added and the mixture was stirred for 3 hours at 40° C under argon. The solvents were removed by repeated concentration in vacuo in the presence of benzene. This gave a crude yield of IA of 0.88 g (slightly yellow oil).

The subsequent column chromatography with ethyl acetate - acetic acid, 97.5:2.5 (on 180 g of Merck silica gel (70 – 230 mesh)) gave the following (individual fractions: 4 ml): in fractions 50 – 80, 256 mg of 15 R-epimer IA, and in fractions 86 – 185, 200 mg of 15 S-epimer IA.

Yield: 0.456 g (75.2%).

Thin layer chromatogram (solvent as for column chromatography):

15 R-epimer $R_f = 0.33$
15 S-epimer $R_f = 0.23$

Nuclear resonance spectra (in CDCl$_3$), $\delta$ - values: (the spectra for the 15 R-epimer and the 15 S-epimer were practically identical, within the scope of the customary resolution): 0.9 singlet 6 H (CH$_3$), 1.15 triplet 3 H (C$\underline{H_3}$—CH$_2$—), 1.3 – 2.6 multiplet 12 H (—C$\underline{H_2}$—> CH—), 3.3 singlet 2 H (—(CH$_3$)$_2$C—C$\underline{H_2}$—O—), 3.45 quartet 2 H (—O—C$\underline{H_2}$—CH$_3$), 3.8 – 4.4 multiplet 3 H (>H$\underline{C}$—OH), 5.20 – 5.7 multiplet 4 H (olefinic H), 5.6 – 5.9 broad singlet 4 H (3 × O$\underline{H}$, 1 × COO$\underline{H}$).

The signal at 5.6 – 5.9 ppm can be removed by H/D exchange.

b. 0.4 g of 9α-hydroxy-11α, 15-dihydroxy-16, 16-dimethyl-18-oxa-5cis-13-trans-20-nor-prostadienoic acid (IA) was prepared in an analogous manner from 0.8 g of 9α-hydroxy-11α, 15-bistetrahydropyramyloxy-16, 16-dimethyl-18-oxa-5cis-13-trans-20-nor-prostadienic acid. Results obtained by column chromatography with ethyl acetate - acetic acid (97.5 : 2.5):

| 120 mg | 15 R -epimer | IA |

| 170 mg | 15 S -epimer | IA | nuclear magnetic resonance in CDCL$_3$: δ-values: (spectra for the 15 R-epimer and 15 S-epimer identical within the scope of the usual resolution).

0.9 singlet 6H(CH$_3$), 1.3–2.4 multiplet 12H (—CH$_2$,>CH), 3.3 singlet (OCH$_2$)—2H, 3.4 singlet 3H (OCH$_3$), 3.7–4.4 multiplet 3H(—CH—OH), 5.2–5.5 multiplet 4H (olefinic protons), 5.7–6.0 broad signal 4H (3 × OH, 1 × COOH).

By exchanging H/D the signal can be eliminated at 5.7–6.0 ppm.

c. 0.8 g of 9α-hydroxy-11α,15-dihydroxy-16,16,20,20-tetramethyl-18-oxa-5cis, 13-trans-prostadienoic acid was prepared in an analogous manner from 1.0 g of 9α-hydroxy-11α, 15-bistetrahydropyramyloxy-16, 16,20,20-tetramethyl-18-oxa-5cis, 13-trans-prostadienic acid.

Results obtained by column chromatography:

360 mg 15 R-epimer IA
260 mg 15 S-epimer IA nuclear magnetic resonance in CDCl$_3$) δ-values: 0.85–1.05 double duplet 12H (CH$_3$), 1.3–2.6 multiplet 13H (CH$_2$,>CH—), 3.2 singlet 2H (OCH$_2$), 3.3 duplet 2H (—OCH$_2$), 3.8–4.4 multiplet 3H (>CH—OH), 5.2–5.7 multiplet 4H (olefinic protons), 5.7–5.9 broad signal 4H (3 × OH, 1 × COOH).

d. 0.2 g of 9α-hydroxy-11α, 15-dihydroxy-16,16-dimethyl-18-oxa-5cis, 13-trans,20,-20-trans-prostatrienoic acid was prepared in an analogous manner from 0.3 g of 9α-hydroxy-11α,15-bistetrahydropyramyloxy-16,16-dimethyl-18-oxa-5-cis-13-trans-20,20-trans-prostatrienic acid. Values obtained by column chromatography:

| 55 mg | 15 R-epimer | I A |
| 50 mg | 15 S-epimer | I A | nuclear magnetic resonance in CDCl$_3$: δ-values: 0.9 singlet 6H (CH$_3$), 1.2–2.6 multiplet 12H (—CH$_2$—,>λ CH—), 3.3 singlet 2H(—OCH$_2$—), 3.35 – 4.3 multiplet 5H(—OCH$_2$—, >CH—OH), 5.0 – 6.3 multiplet 11H (olefinic protons, 3 × OH, 1 × COOH).

EXAMPLE 10

Synthesis of
9-oxo-11α,15-ditetrahydropyranyloxy-16,16-dimethyl-18-oxa-5-cis-13-trans-prostadienoic acid
(16,16-dimethyl-18-oxa-PGE$_{2α}$-11,15-bis-tetrahydropyranyl ether) (XI)

0.85 g of the compound Xa is dissolved in 30 ml of acetone. 2 ml of Jones reagent (2.1 g of chromic acid, 6 ml of water and 1.7 ml of concentrated sulphuric acid) are added dropwise under argon at −20° to −25° C. The mixture is stirred for 30 minutes, 3 ml of isopropanol are then added and the whole is stirred for a further 10 minutes in order to destroy excess oxidation reagent. 100 ml of methylenechloride and 100 ml of water were then added, the mixture was extracted by shaking, the phases were separated, the organic extract was dried with MgSO$_4$ and the solvent was concentrated in vacuo at a maximum of +5° C. The yield of the compound XI was 0.72 g of an almost colorless, clear oil (85%).

Thin layer chromatogram (ethyl acetate - acetic acid = 97.5:2.5): R$_f$ = 0.69.

Absorptions in the infrared spectrum (NaCl plates): 2,950, 1,745 (ketone-carbonyl), 1,720 (acid-carbonyl), 1,115, 1,040 and 970.

EXAMPLE 11 a. Synthesis of
9-oxo-11α,15-dihydroxy-16,16-dimethyl-18-oxa-5-cis-13-trans-prostadienoic acid
(16,16-dimethyl-18-oxa-PGE$_{2α}$)

15 S- and 15 R-epimers (IB)

0.72 g of the compound XIa as dissolved in 5 ml of tetrahydrofurane, 15 ml of acetic acid - water, in the ratio of 2:1, were added and the mixture was stirred for 4 hours at 40° C. The solvent was then removed in vacuo with repeated addition of benzene, during which the temperature should not exceed +5° C. The yield of the compound I B was 0.6 g of a light oil. After column chromatography on Merck silica gel (70 - 230 mesh) with chloroform - methanol = 22:1 (individual fractions of 2 ml), fractions 130 - 170 give 104 mg of 15 R-epimer I B and fractions 170 - 280 give 102 mg of 15 S-epimer I B.

Yield: 0.206 g (41.5%).

Thin layer chromatogram (solvent: ethyl acetate - acetic acid = 97.5:2.5) (Merck silica gel plates)

R$_f$ = 0.36 15 R-epimer
R$_f$ = 0.28 15 S-epimer

The spectra for the 15 R-epimer and 15 S-epimer of I B are practically identical within the scope of the customary resolution.

Absorptions in the infrared spectra (NaCl plates): 3,450 (OH band), 2,950, 1,745 (ketone-carbonyl), 1,720 (acid-carbonyl), 1,110, 1,040 and 970.

Nuclear resonance spectrum (in CDCl$_3$), δ - values: 0.9 singlet 6 H (CH$_3$), 1.18 triplet 3 H (C$\underline{H}_3$CH$_2$—), 1.4 – 2.7 multiplet 12 H (—CH$_2$—,>CH—), 3.28 singlet 2 H (—(CH$_3$)$_2$C—CH$_2$—O—), 3.46 quartet 2 H (—OCH$_2$CH$_3$), 3.8 – 4.4 multiplet 2 H (>C$\underline{H}$—OH), 5.25 – 5.75 multiplet 4 H (olefinic H), 5.9 – 6.4 broad singlet 3 H (2 × O$\underline{H}$, 1 × COO$\underline{H}$).

The signal at 5.9 – 6.4 ppm can be removed by H/D exchange.

b. 2.0 g of 9-oxo-11α, 15-dihydroxy-16,16-dimethyl-18-oxa-5cis-13-trans-20-nor-prostadienoic acid (IB) were prepared in an analogous manner from 3.8 g of 9-oxo-11α, 15-bis-tetrahydropyramyloxy-16,16-dimethyl-18-oxa-5cis-13-trans-20 nor-prostadienic acid. Results obtained by column chromatography:

| 800 mg | 15 - R-epimer | (IB) |
| 750 mg | 15 - S-epimer | (IB) | nuclear magnetic resonance in CDCl$_3$: δ-values: 0.9 singlet 6H (CH$_3$), 1.3–2.8 multiplet 12H(—CH$_2$—>λ CH—), 3.25 singlet 2H (OCH$_2$), 3.35 singlet 3H (OCH$_3$), 3.8 – 4.3 multiplet 3H >—CH—OH), 5.2 – 5.8 multiplet 4H (olefinic protons), 6.5 - 6.8 broad singlet 3H (2 × OH, COOH)

c. 1.9 g of 9-oxo-11α, 15-hydroxy-16,16,20,20-tetramethyl-18-oxa-5cis-13-trans-prostadienic acid (IB) were prepared in an analogous manner from 4.9 g of 9-oxo-11α, 15-bistetrahydropyramyloxy-16,16,20,20-tetramethyl-18-oxa-5cis-13-trans-prostadienoic acid.

Nuclear magnetic resonance in CDCl$_3$: δ-values: 0.90 – 1.1 double singlet 12H (CH$_3$), 1.3 – 2.8 multiplet 13H (CH$_2$, >CH—) 3.2 singlet 2H (OCH$_2$), 3.4 duplet 2H (—O—CH$_2$—), 3.6 – 4.3 multiplet 3H (>CHOH), 5.3 – 5.8 multiplet 4H (olefinic protons), 5.9 – 6.5 broad singlet 3H (2 × OH, COOH).

EXAMPLE 12

Synthesis of 9α,11α,15-trihydroxy-16,16-dimethyl-18-oxa-prostanoic acid (I C)

50 mg of 5% strength palladium/animal charcoal catalyst were pre-hydrogenated for 1 hour in 5 ml of ethanol. 70 mg of the compound I A (15 R-epimer) in 15 ml of ethanol were then added and hydrogenation was completed over the course of 3 hours at room temperature. The hydrogen absorption was 12.5 ml. The catalyst was filtered off and the filtrate was concentrated in vacuo.

Yield of the compound I C: 70 mg of colorless oil (98%).

Thin layer chromatogram (ethyl acetate - acetic acid, 97.5:2.5), R$_f$ = 0.26, 15 R-epimer. (An identical charge was also run with the 15 S-epimer of I A).

Nuclear-magnetic resonance (in CDCl$_3$), δ - values: 0.95 singlet 6 H (CH$_3$—), 1.21 triplet 3 H (CH$_3$CH$_2$—), 1.1 – 2.5 multiplet 20 H (—CH$_2$—, >CH—), 3.32 singlet 2 H (—(CH$_3$)$_2$—C—CH$_2$—O—), 3.52 quartet 2 H (—O—CH$_2$—CH$_3$), 3.7 – 4.4 multiplet 3 H (>CH—OH), 6.1 – 6.7 broad singlet 4 H (3 × OH, 1 × COOH).

The signal at 6.1 – 6.7 ppm can be removed by H/D exchange.

EXAMPLE 13

Synthesis of 9-oxo-11α,15α-dihydroxy-16,16-dimethyl-18-oxa-prostanoic acid (I D)

70 mg of the compound I B were hydrogenated as under Example 12. 6.5 mg of colorless oil (93%) are obtained.

Nuclear magnetic resonance (in CDCl$_3$), δ - values: 0.92 singlet 6 H (CH$_3$), 1.20 triplet 3 H (CH$_3$CH$_2$), 1.2 – 2.5 multiplet 20 H (—CH$_2$—, >CH—), 3.30 singlet 2 H (—(CH$_3$)$_2$C—CH$_2$—O—), 3.50 quartet 2 H (—O—CH$_2$—CH$_3$), 3.8 – 4.4 multiplet 2 H (>CH—OH), 5.8 – 6.2 broad singlet 3 H (2 × OH, 1 × COOH).

The signal at 5.8 – 6.2 ppm can be removed by H/D exchange.

Thin layer chromatogram (ethyl acetate - acetic acid, 97.5: 2.5): R$_f$ = 0.35.

What is claimed is:

1. 9-oxo-11α,15-dihydroxy-16,16-dimethyl-18-oxa-5-cis-13-trans-prostadienoic acid.

2. 9-oxo-11α,15-hydroxy-16,16-dimethyl-18-oxa-5-cis-13-trans-20-nor-prostadienoic acid.

3. 9-oxo-11α,15-dihydroxy-16,16,20,20-tetramethyl-18-oxa-5-cis-13-trans-prostadienoic acid.

* * * * *